United States Patent
Hinchliffe et al.

(10) Patent No.: US 8,968,388 B2
(45) Date of Patent: *Mar. 3, 2015

(54) DEVICE FOR REGULATING BLOOD FLOW

(75) Inventors: Peter W. J. Hinchliffe, Campbell Hall, NY (US); Menno Kalmann, Elspeet (NL); Adam I. Lehman, Northford, CT (US)

(73) Assignee: Deep Vein Medical, Inc., Canton, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 13/367,013

(22) Filed: Feb. 6, 2012

(65) Prior Publication Data

US 2012/0136429 A1    May 31, 2012

Related U.S. Application Data

(63) Continuation of application No. 12/713,476, filed on Feb. 26, 2010, now Pat. No. 8,109,993, which is a continuation-in-part of application No. 12/319,176, filed on Jan. 2, 2009, now Pat. No. 8,092,517, and a continuation-in-part of application No. 11/801,489, filed on May 10, 2007, now abandoned, and a continuation-in-part of application No. 11/801,691, filed on May 10, 2007, now Pat. No. 7,811,316.

(60) Provisional application No. 61/156,227, filed on Feb. 27, 2009, provisional application No. 61/010,012, filed on Jan. 4, 2008, provisional application No. 60/808,406, filed on May 25, 2006, provisional application No. 60/809,483, filed on May 31, 2006.

(51) Int. Cl.
*A61F 2/82* (2013.01)
*A61F 2/24* (2006.01)

(52) U.S. Cl.
CPC .............. *A61F 2/2418* (2013.01); *A61F 2/2475* (2013.01); *A61F 2220/005* (2013.01); *A61F 2220/0058* (2013.01); *A61F 2220/0075* (2013.01); *A61F 2230/0054* (2013.01)
USPC .......................................................... 623/1.24

(58) Field of Classification Search
USPC ......................................... 623/1.24, 2.1–2.19
See application file for complete search history.

(56) References Cited

U.S. PATENT DOCUMENTS

| | | | | |
|---|---|---|---|---|
| 5,607,465 | A * | 3/1997 | Camilli ......................... | 623/1.24 |
| 7,758,632 | B2 * | 7/2010 | Hojeibane et al. ........... | 623/1.24 |
| 7,811,316 | B2 * | 10/2010 | Kalmann et al. ............. | 623/1.24 |
| 8,109,993 | B2 * | 2/2012 | Hinchliffe et al. ........... | 623/1.24 |
| 2007/0276467 | A1 * | 11/2007 | Kalmann ...................... | 623/1.24 |
| 2012/0083900 | A1 * | 4/2012 | Samaniego et al. ........ | 623/23.72 |
| 2013/0202675 | A1 * | 8/2013 | Ericson ......................... | 424/443 |

* cited by examiner

*Primary Examiner* — Suzette J Gherbi
(74) *Attorney, Agent, or Firm* — Brown Rudnick LLP; Thomas C. Meyers

(57) ABSTRACT

An implantable device for regulating blood flow through a blood vessel includes an elongated support. The support includes axially spaced apart first and second substantially annular support portions, and an x-shaped linking member linking the axially spaced apart portions to one another. The device also includes a valve membrane extending between the axially spaced apart support portions and having an upper portion, a lower portion and an intermediate portion. The valve membrane includes a first region and a second lower region. The first region is folded over the linking member for attachment and the second region is adjacent the first region and unattached to the linking member. The second region is movable between a first position to enable blood flow and a second position to inhibit blood flow.

20 Claims, 12 Drawing Sheets

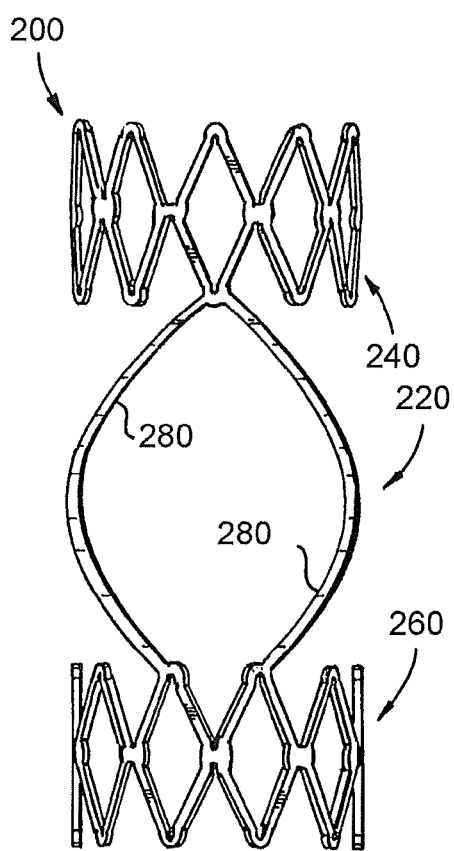
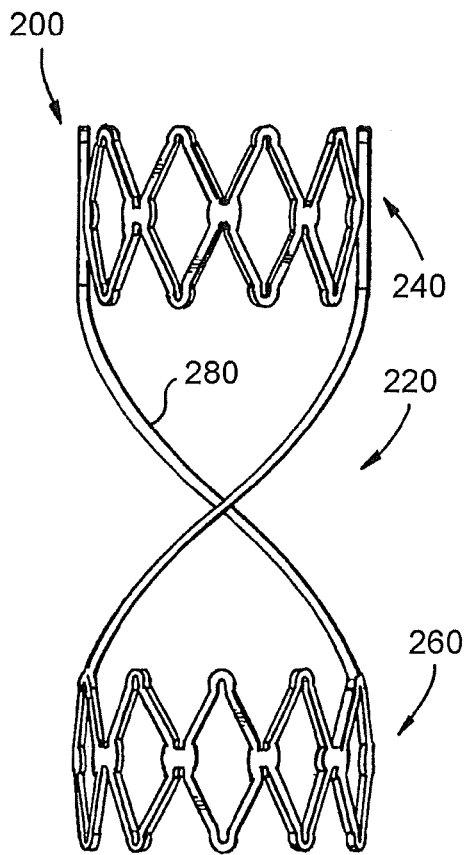
Fig. 9
Fig. 10
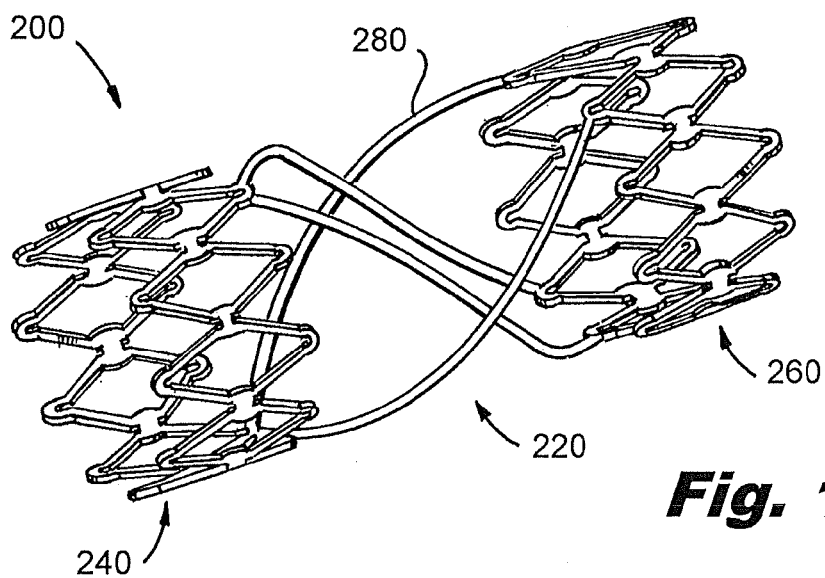
Fig. 11

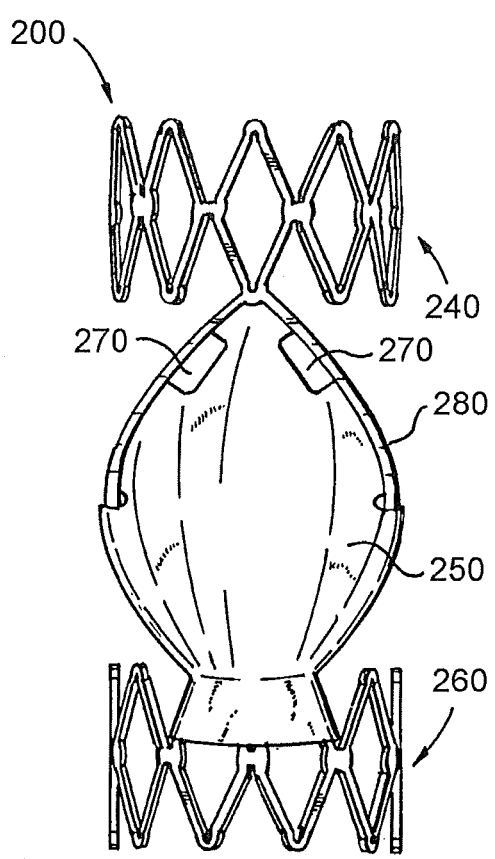
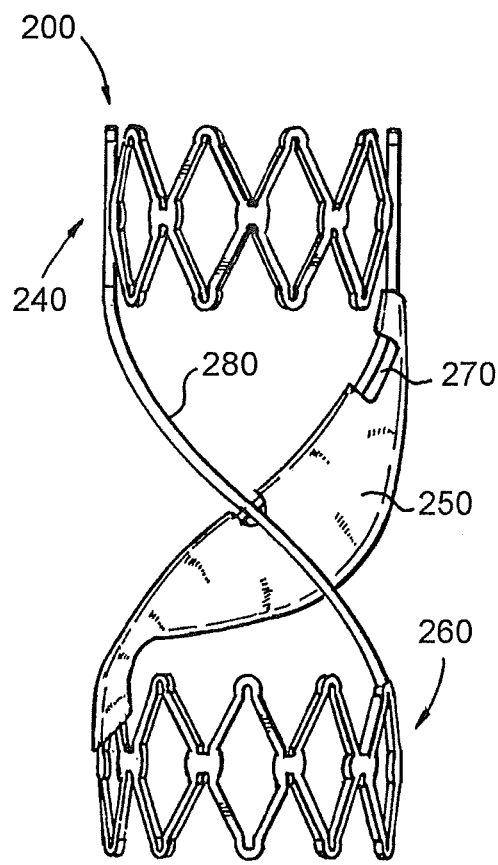
*Fig. 12*    *Fig. 13*
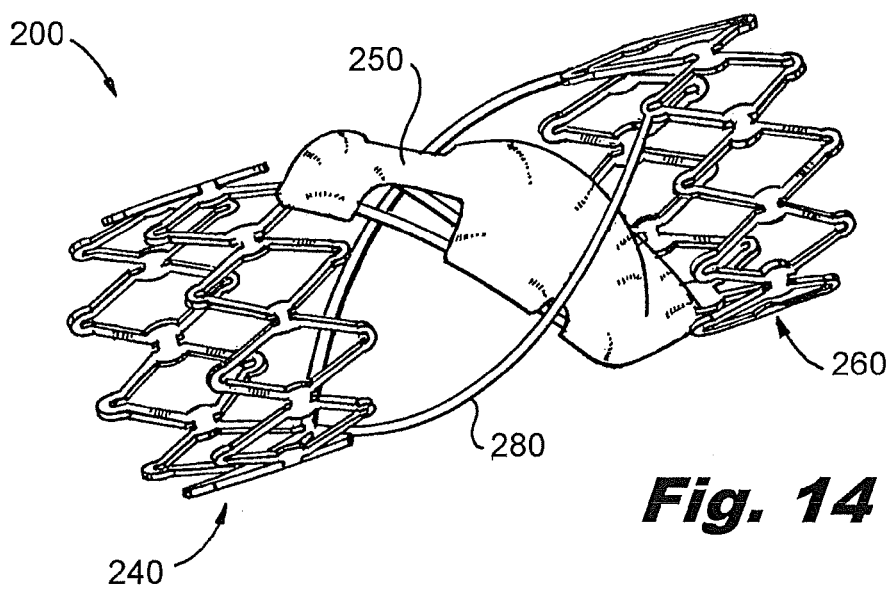
*Fig. 14*

DEVICE FOR REGULATING BLOOD FLOW

CROSS-REFERENCE TO RELATED APPLICATIONS

This application is a continuation of U.S. patent application Ser. No. 12/713,476 filed Feb. 26, 2010, which is a continuation-in-part of U.S. patent application Ser. No. 12/319,176 filed Jan. 2, 2009, and which claims benefit of priority to U.S. Provisional Patent Application Ser. No. 61/156,227 filed Feb. 27, 2009. U.S. patent application Ser. No. 12/319,176 claims benefit of priority to U.S. Provisional Patent Application Ser. No. 61/010,012 filed Jan. 4, 2008 and is a continuation-in-part of both U.S. patent application Ser. No. 11/801,489 filed May 10, 2007, and Ser. No. 11/801,691 filed May 10, 2007 (now U.S. Pat. No. 7,811,316), each of which claim benefit of priority to U.S. Provisional Application Ser. No. 60/808,406 filed May 25, 2006 and 60/809,483 filed May 31, 2006. The content of each of the applications listed above is incorporated by reference herein in its entirety.

BACKGROUND OF THE INVENTION

1. Field of the Invention

The subject invention is directed to a device for regulating blood flow in the venous system, and more particularly, to an implantable valve device for regulating the flow of blood through a blood vessel.

2. Description of Related Art

The blood system, and in particular the venous blood system of the legs and arms is provided with valves that are uniquely located in a manner so as to ensure that blood will not flow back upstream in the direction from which it has been pumped from the heart. In the arms and legs, there is a deep venous system and a surface (superficial) venous system. Due to various causes, thrombosis can occur in the deep venous system. Blood thinning can alleviate this problem. However, valves do not effectively close and often leak when the blood in thinned. This can cause increased venous blood pressure in the direction of the ankles, which can lead to a variety of problems including pain, swelling, varicose veins and ulcers. Complaints of this type are wide spread among those who spend prolonged periods of time in a standing position, for instance, surgeons.

The surface venous system of the leg is relatively weaker than the deep venous system, and it has the tendency to spontaneously widen due to the increased pressure of blood from above. This widening prevents the valves from functioning effectively and can lead to varicose veins, which are both unattractive and painful. Major surgery is often required to treat these blood vessel problems. For example, varicose veins are treated by either closing off the vein, which leads to a reduced blood flow capacity and increased pressure on surrounding blood vessels to ensure blood drainage, or by completely removing the varicose veins, which leads to the same problem. The deep veins require invasive surgery and because of the swelling, risk of infection and trauma is seldom attempted. In either case, the treatment of the surface veins does not treat the failed valves in the deep system, thereby causing the continued pressure and back flow into the legs. The subject invention is directed to a device for obviating problems of this type.

SUMMARY OF THE INVENTION

The subject invention is directed to a new and useful implantable device for regulating blood flow through a blood vessel. The device includes an elongated support dimensioned and configured to be implanted in a blood vessel. The support includes axially spaced apart first and second substantially annular support portions, and an x-shaped linking member linking the axially spaced apart portions to one another. The device also includes a valve membrane extending between the axially spaced apart support portions and having an upper portion, a lower portion and an intermediate portion. The valve membrane includes a first region and a second lower region. The first region is folded over the linking member for attachment and the second region is adjacent the first region and unattached to the linking member. The second region is movable between a first position to enable blood flow and a second position to inhibit blood flow.

In certain embodiments, the device further includes a third region folded over for attachment to the linking member, with the second region positioned between the first and third regions. The linking member can include two curved members intersecting one another to form an x-shape. The support can be formed at least in part from a shape memory alloy material, or any other suitable material. The valve membrane can be formed at least in part from ePTFE, or any other suitable material. It is also contemplated that the valve membrane can be coated at least in part with an anti-clotting agent.

In accordance with certain embodiments, the device further includes a second x-shaped linking member. The valve membrane can include a fourth region folded over the second linking member for attachment. The upper portion of the valve membrane can be attached to a bottom region of the first support portion and the lower portion of the membrane can be attached to a top region of the second support portion. A section of the lower portion of the membrane can be wrapped around a section of the top region of the second support portion. It is contemplated that the support can be integrally formed from a laser cut tube.

In accordance with certain embodiments, a first x-shaped linking member links the axially spaced apart portions to one another, and a second x-shaped linking member opposed to the first linking member also links the axially spaced apart portions to one another. The valve membrane can include first, second and third portions wherein the first portion is attached at a first region of the support, the third portion is attached at a second region of the support, and the second portion is positioned between the first and third portions and is unattached to the support. The second portion can thus be movable with respect to the support between a first position to enable blood flow and a second position closer to the support to inhibit blood flow.

It is contemplated that in certain embodiments, the first and a third portions of the valve membrane can form a flap wrapped around a portion of the support, and the second portion can form a flap movable with respect to the first and third portions to create an opening for antegrade blood flow. The second portion of the valve membrane can be closer to a top region than to a bottom region of the valve membrane.

In certain embodiments, the valve membrane further includes a fourth portion separate from the second portion and unattached to the support. The fourth portion is movable with respect to the support between a first position to enable blood flow and a second position to inhibit blood flow. The second portion can form a first flap adjacent the first linking member and the fourth portion can form a second flap adjacent the second linking member. The flaps can each create a space between the respective flap and the respective linking member during antegrade blood flow to enable blood flow through the space and the respective flap closing the space during retrograde blood flow.

The valve membrane can be attached to the linking member, wherein the valve membrane has an upper portion attached to a first section of the support and a lower portion attached to a second section of the support. The valve membrane can have an enabling condition to enable blood flow when blood flows in one direction and an inhibiting condition to inhibit blood flow when blood flows in an opposite direction. The upper attached portion of the membrane and the lower attached portion of the membrane can remain substantially fixed in position in both the enabling condition and the inhibiting condition and the lower and upper attached portions can remain adjacent opposing regions of the vessel wall in both conditions.

In certain embodiments, the valve membrane includes an intermediate portion between the upper and lower attached portions, and further includes a first flap in the intermediate portion. The first flap can be unattached to the support and can be movable for creating the flow inhibiting and flow enabling conditions while the upper and lower attached portions remain substantially fixed in position.

It is contemplated that the valve membrane can have a first region unattached to the support, wherein the first unattached region is formed by at least one cut in the membrane. The first unattached region can create a first opening adjacent the support during antegrade blood flow. The valve membrane can also have a second region unattached to the support, the second unattached region being formed by at least one cut in the membrane. The second unattached region can create a second opening adjacent the support during antegrade blood flow. It is contemplated that the first and second openings can create a cross sectional shape ranging from about 15% to about 30% of the diameter of the vessel.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the apparatus of subject invention without undue experimentation, preferred embodiments thereof will be described in detail hereinbelow with reference to certain figures, wherein:

FIG. 9 is a front elevation view of the frame of a flow-regulating device constructed in accordance with another embodiment of the subject invention with the membrane or sail removed for clarity;

FIG. 10 is a side elevation view of the frame of FIG. 9, showing one of the symmetrical x-shaped linking members connecting the two axially spaced apart ring portions;

FIG. 11 is a perspective view of the frame of FIG. 9, showing both of the symmetrical x-shaped linking members;

FIG. 12 is a front elevation view of the flow-regulating device of FIG. 9, showing the membrane or sail in place;

FIG. 13 is a side elevation view of the flow-regulating device of FIG. 12, showing one of the symmetrical x-shaped linking members connecting the two axially spaced apart ring portions with the membrane or sail attached to a portion of the cross members of the x-shaped linking member; and FIG. 14 is a perspective view of the flow-regulating device of FIG. 12, showing both of the symmetrical x-shaped linking members with the membrane or sail in place, shown in the flow restricting position.

DETAILED DESCRIPTION OF THE PREFERRED EMBODIMENTS

Figure 1:
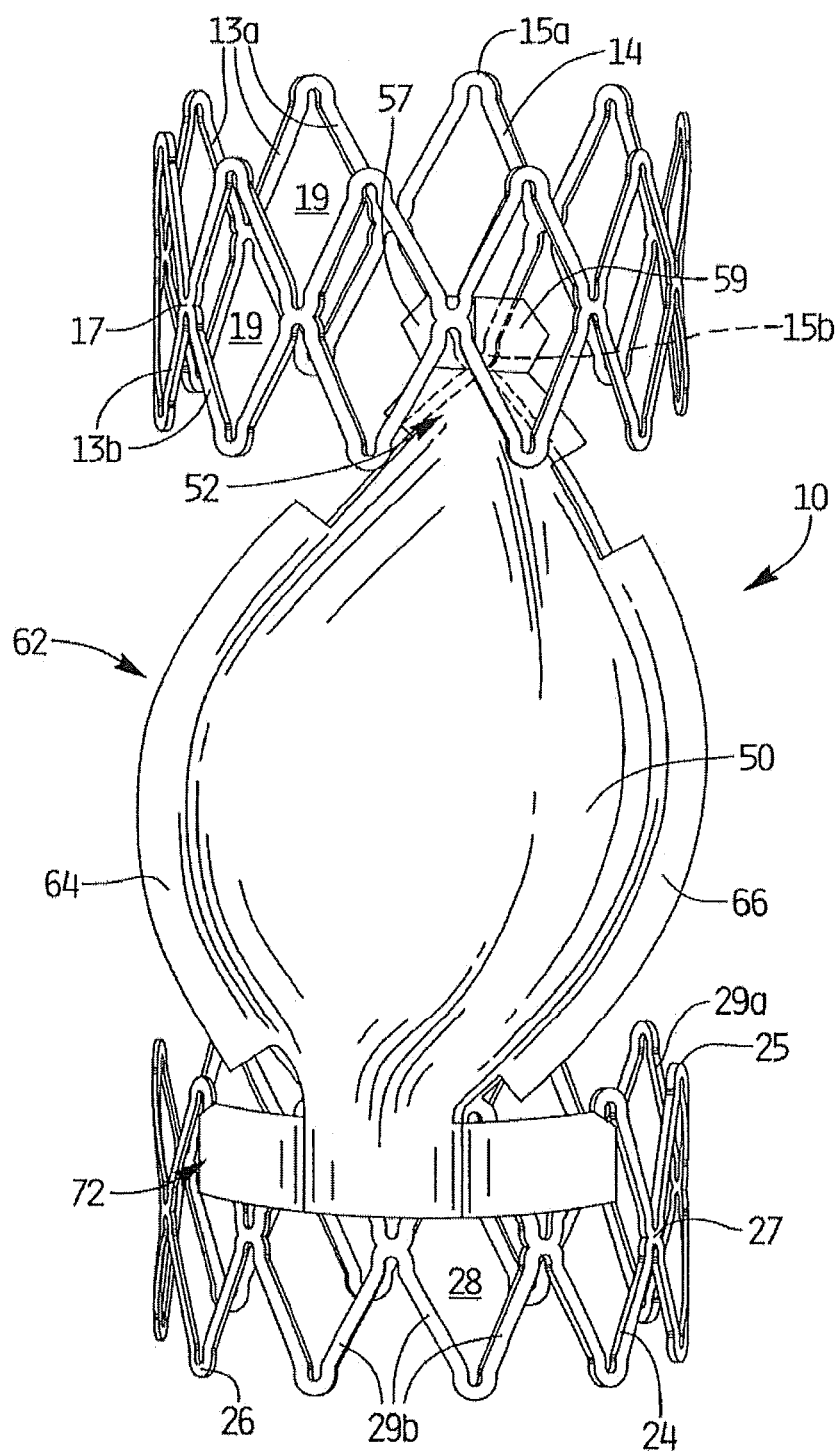
FIG. 1 is a perspective view of the flow regulating device of the present invention, prior to full assembly.

Referring now to the drawings wherein like reference numerals identify similar or like components throughout the several views, there is illustrated a flow regulating device constructed in accordance with a preferred embodiment of the subject invention, and designated generally by reference numeral 10. Regulating device 10 includes an elongated support 12 that has upper and lower substantially annular ring portions 14 and 24, each having a series of rounded V-shaped apices 15a facing in an upward direction and a series 15b facing in a downward direction. That is, the upper or distal (with respect to the direction of blood flow) ring portion 14 has a first series of angled struts 13a forming a V and a second series of angled struts 13b forming an inverted V which together form a group of closed substantially diamond shaped cells 19 connected at region 17. Similarly, the lower or proximal (with respect to the direction of blood flow) ring portion 24 has a first series of angled struts 29a and a second series of angled struts 29b, facing in opposite directions and forming closed substantially diamond shaped cells 28 connected at region 27. The cells 28 have upper apices 25 and lower apices 26. For clarity, not all of the identical parts in the drawings are labelled. Note that in the preferred embodiment, the rings and linking member (described below) are preferably integral so that terms "joined", "connected", etc. are used for ease of description.

Figure 2:
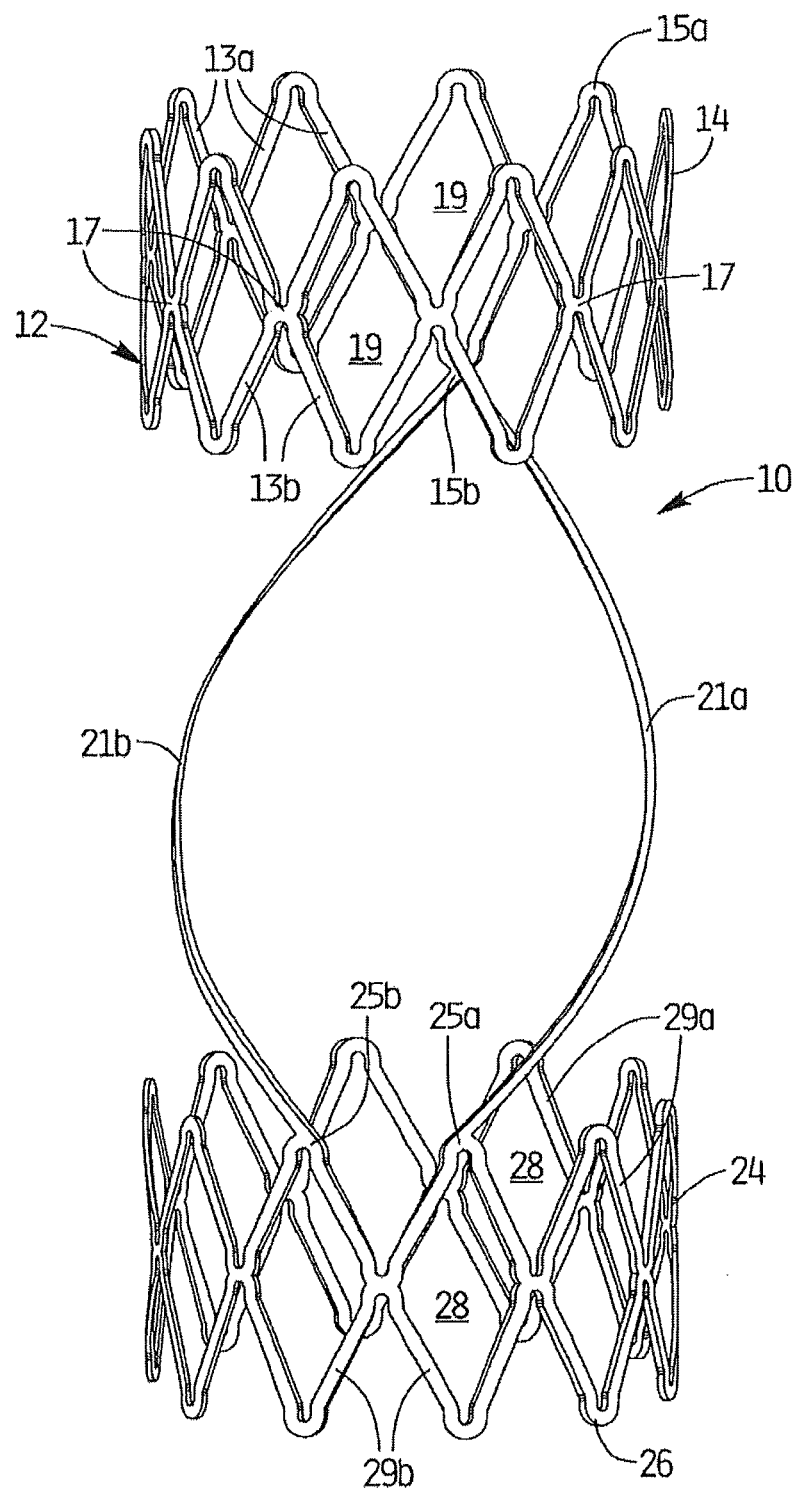
FIG. 2 is a perspective view of the support of the flow-regulating device of FIG. 1.

Support 12 has two curved linking or connecting members 21a, 21b, best shown in FIG. 2 in which the membrane is removed for clarity. The top of each connecting member 21a, 21b extends from a common lower apex 15b of one of the pairs of angled struts 13b of upper ring 14 (see also FIGS. 3 and 4) The lower end of connecting members 21a, 21b extend from separate upper apices 25a, 25b, respectively, of cells 28 of lower ring 24. In the illustrated embodiment, the apices 25a, 25b, are about 36 degrees apart as ten cells are formed. However, a different number of cells can be provided with different spacing between apices. Also, it should be appreciated that the connecting members can extend from other apices of lower ring 24 or upper ring 14. The connecting members 21a, 21b have a curve or twist extending close to about 180 degrees (and extending substantially across the vessel when implanted) so that an upper end is connected to one end (viewed radially/transversely) of the device 10 and the lower end is connected to an opposite end (viewed radially/transversely) of the device 10. That is, with ten closed cells in the illustrated embodiment, apex 15b is approximately 162 degrees out of phase from apex 25a and from apex 25b. Other spacing and alternate number of cells is also contemplated.

Although two connecting members are shown, one connecting member or more connecting members could be provided. Also, the connecting members could be spaced further or closer apart and have different curves than shown.

The rings 14, 24 are collapsed to a reduced diameter (profile) position for delivery. The rings 14, 24, when implanted, are substantially perpendicular to the direction of blood flow. Preferably, the rings 14, 16 in their expanded (deployed) configuration are larger in diameter than the internal diameter of the target vessel to apply a sufficient radial force against the vessel to ensure that the device remains in a desired position and orientation after implantation. For example, for use in an 8 mm vessel, the rings could have an expanded outer diameter of about 10 mm and preferably could be collapsed sufficiently to be delivered through a 12 Fr (4 mm) delivery catheter. Others ring diameters are also contemplated.

The support 12 is preferably composed of shape memory material, such as Nitinol or Elgiloy, with a shape memorized larger diameter configuration as shown in the drawings. In the illustrated embodiment, the support is laser cut from a tube so that the connecting members and rings are integral. However, it is also contemplated that alternatively the support can be formed from wire(s). Also, it should be appreciated that instead of being integral, separate members could be provided, with separate rings joined by separate linking (connecting) members.

Device 10 includes a valve member or membrane 50 that is operatively associated with support 12 for regulating the flow of blood through a vessel by moving between open and closed positions. Membrane 50 is preferably formed from a sheet of ultra thin membrane material such as a ePTFE material or the like. It is envisioned that the membranes disclosed herein could be bonded or otherwise coated with an anti-clotting or anti-coagulant/anti-thrombogenic agent such as Heparin and/or an anti-proliferative coating, to retard the body's desire to reject the implant. In a preferred embodiment, the membrane is coated with an anti-thrombogenic agent and the frame is coated with an anti-proliferative agent, such as Dexamethasone by way of example.

Figure 3:
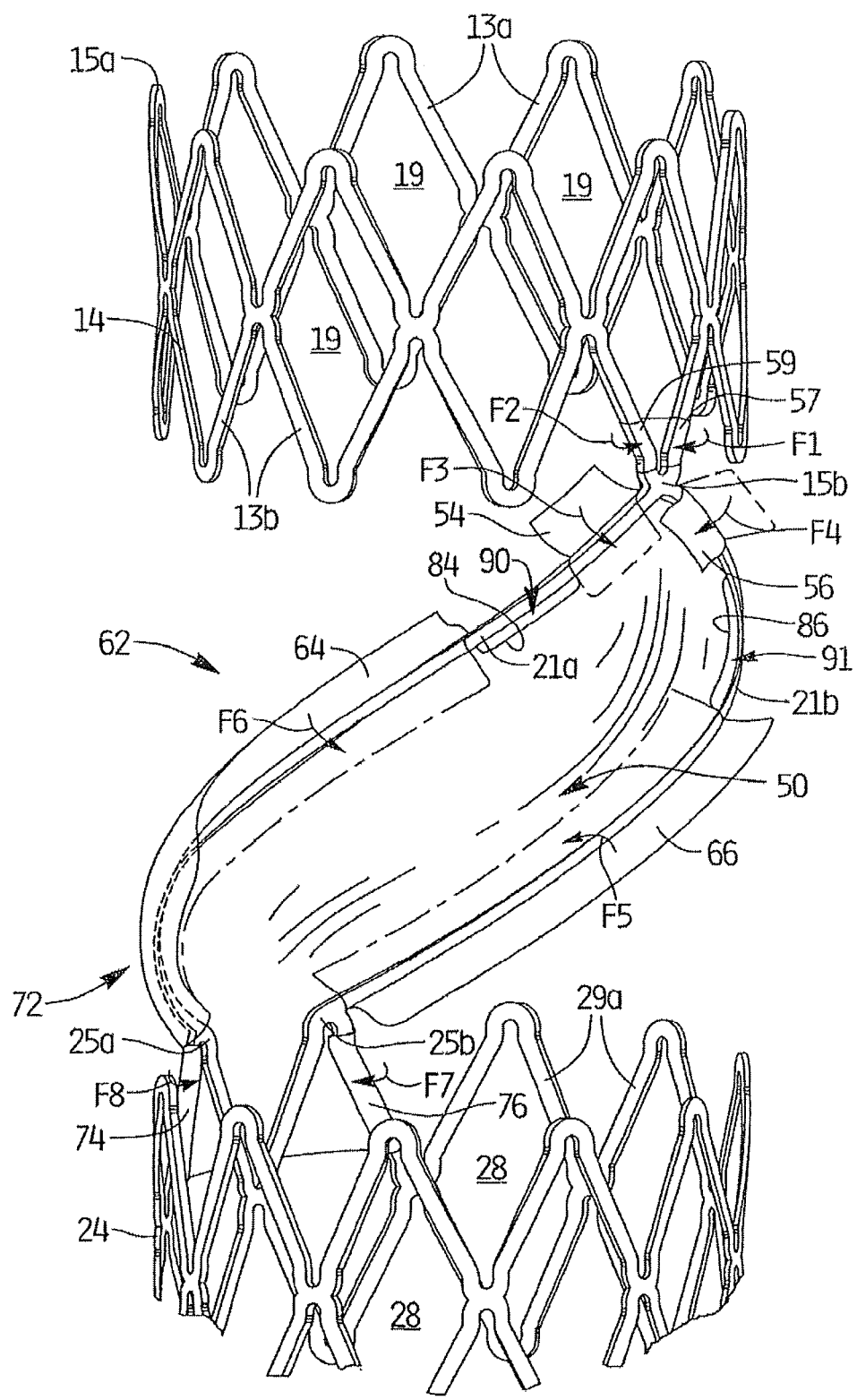
FIG. 3 is a side perspective view of the flow regulating device illustrating how the membrane is attached to the frame.
Figure 4:
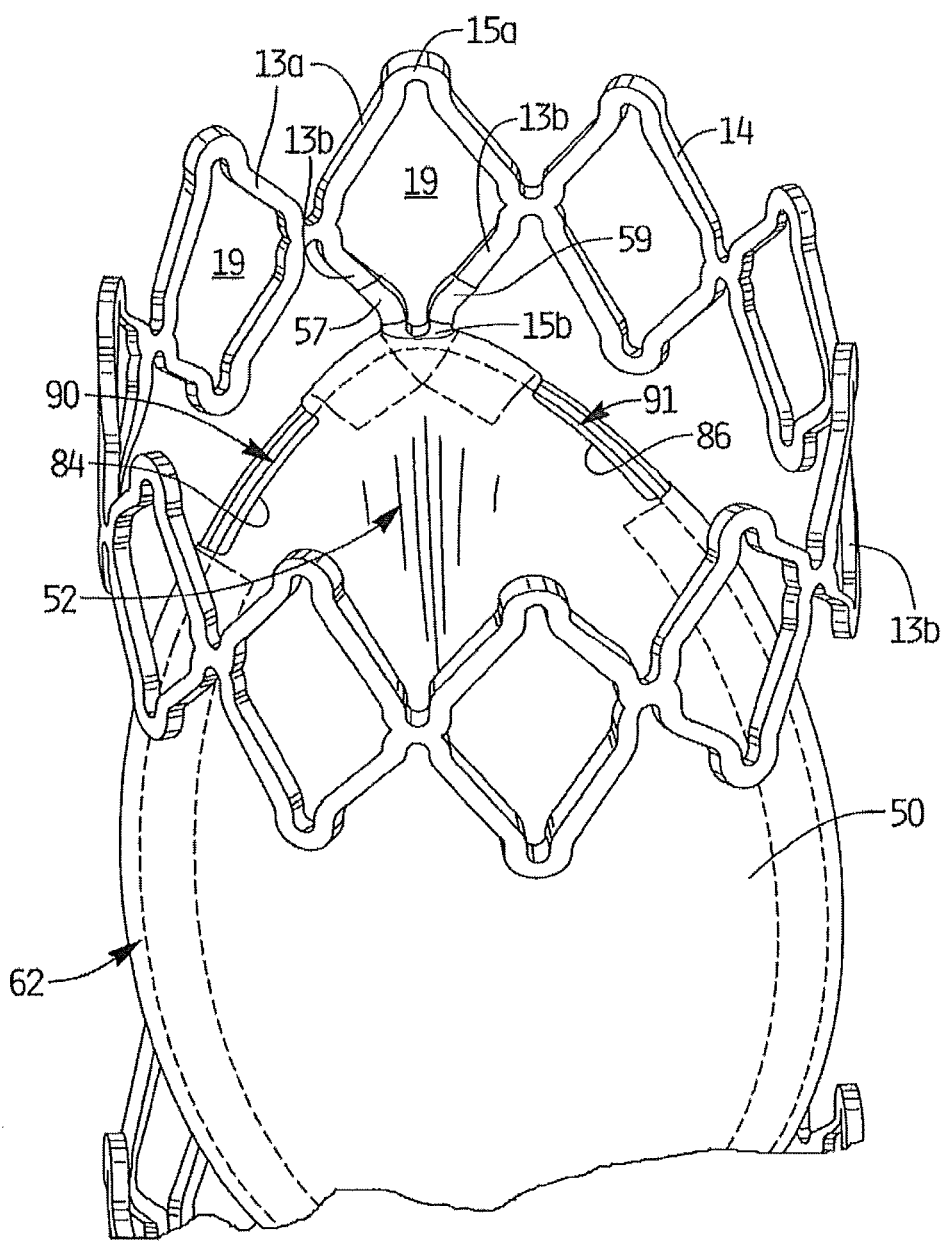
FIG. 4 is a front perspective view of the top (distal) portion of the flow regulating device of FIG. 1 showing the membrane in the closed position.

As shown, valve membrane 50 has an upper portion 52, an intermediate portion 62, and a lower portion 72. With reference to FIG. 3 which illustrates how the membrane 50 is attached to support 12 in manufacture, the top portion 52 has first and second flaps 54, 56 which are folded down over respective connecting members 21a, 21b and attached to the membrane to secure the upper portion 52 of membrane 50 about the support 12. FIG. 3 illustrates flap 56 already folded in the direction of arrow F4 from its unfolded position shown in phantom. FIG. 3 also illustrates flap 54 in its unfolded position before movement in the direction of arrow F3 in manufacture to its folded position depicted in phantom. Flaps 57 and 59 at the uppermost region of membrane 50 are wrapped around struts 13b in the direction of arrows F1, F2, respectively.

With continued reference to FIG. 3, the intermediate portion 62 of membrane 50 has flaps 64, 66 for connection to linking (connecting) members 21a, 21b, respectively. Flap 64 is shown in a mostly unfolded position to be folded in the direction of arrows F6 to its folded position shown in phantom where it is attached to the membrane 50. Flap 66 is shown in its unfolded position to be folded in the direction of arrows F5 to its folded position depicted in phantom.

Lower portion 72 of membrane 50 has flaps 74 and 76 which are each folded around a separate strut 29a. Arrows F8, F7, respectively, illustrate the direction of the fold.

Cuts in the membrane 50 create an unattached flap 84 between upper attached flap 54 and intermediate attached flap 64 and an unattached flap 86 between upper attached flap 56 and intermediate attached flap 66. These unattached flaps 84, 86 are positioned adjacent the respective connecting member 21a, 21b as shown, but create a respective opening 90, 91 for blood flow between the membrane 50 and connecting members 21a, 21b as described below. Note, alternatively, the flaps 84, 86 can extend over the connecting member, as long as it remains unattached and creates a sufficient space from the linking member to create a sufficiently sized opening to allow blood flow therethrough.

Note that FIG. 1 shows the membrane 50 with the flaps open, prior to connection in manufacture, to illustrate how it is wrapped around the support 12 and connected to other portions of the membrane for securement/attachment of the membrane to the support 12. The flaps, after wrapping over/around the region of support 12, can be connected to the membrane body by welding, adhesive, suturing or other methods. Also, an intermediary material can be used to facilitate welding, such as polyurethane or polycarbonate/polyurethane impregnated or otherwise combined with the ePTFE material. It is also contemplated that the membrane can be attached to the support 12 itself by methods such as by adhesive or use of suture material.

Figure 6A:
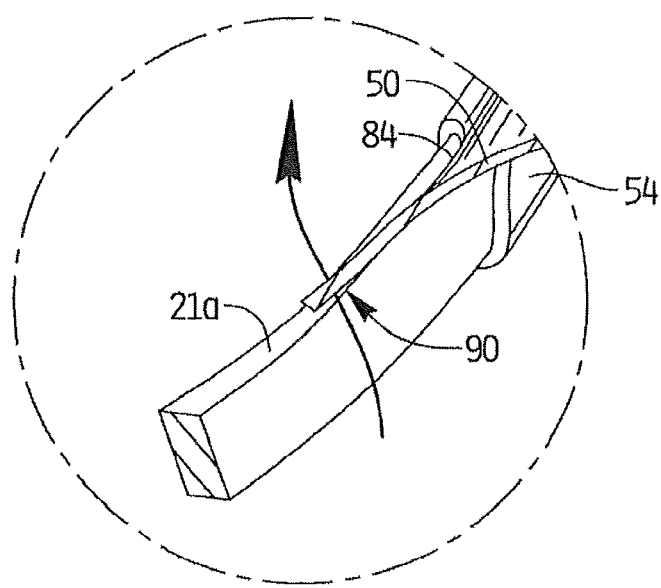
FIG. 6A is a cross-sectional view of the identified area of FIG. 5A showing the membrane in the open position, resulting from antegrade blood flow.
Figure 6B:
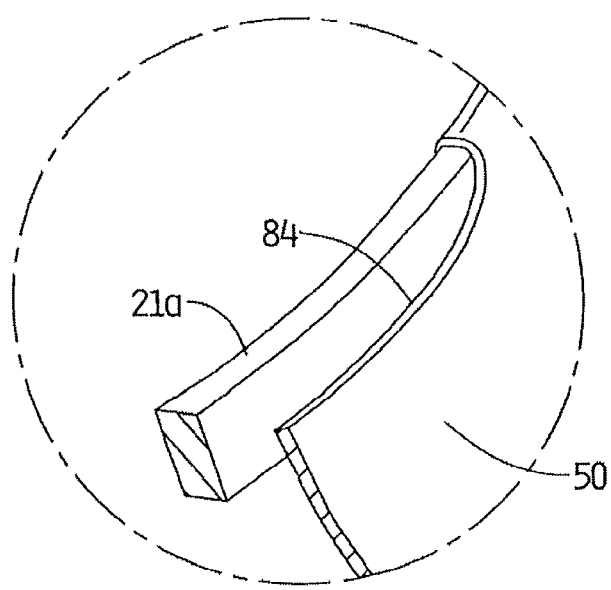
FIG. 6B is a cross-sectional view of the identified area of FIG. 6A showing the membrane in the closed position, resulting from retrograde blood flow.
Figure 6C:
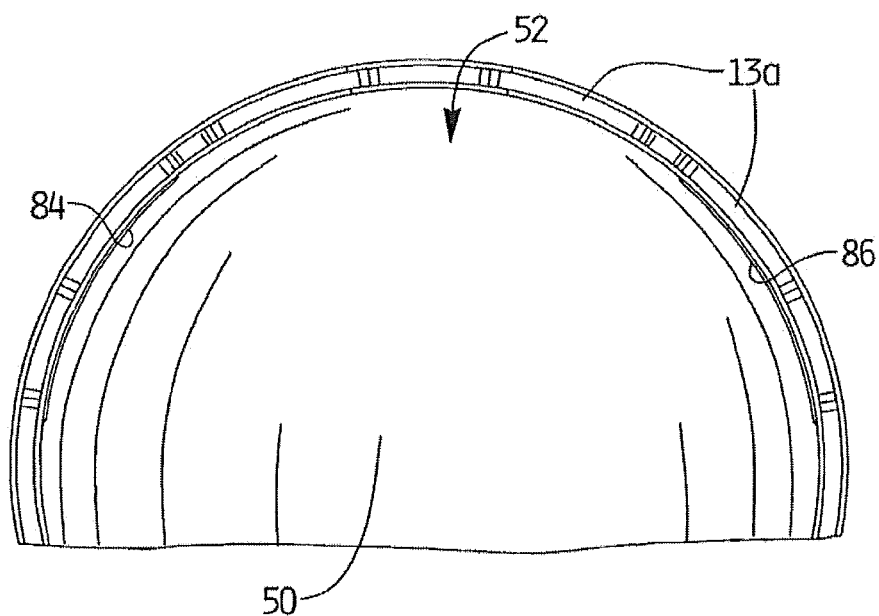
FIG. 6C is a top view of the upper region of the membrane of FIG. 5B showing the membrane in the closed position.
Figure 6D:
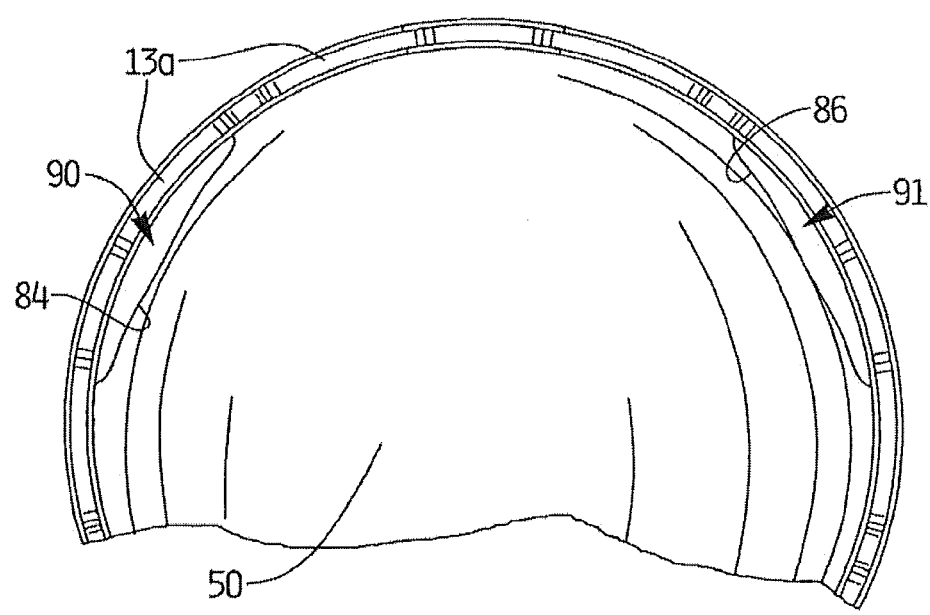
FIG. 6D is a top view of the upper region of the membrane of FIG. 5A showing the membrane in the open position.
Figure 6E:
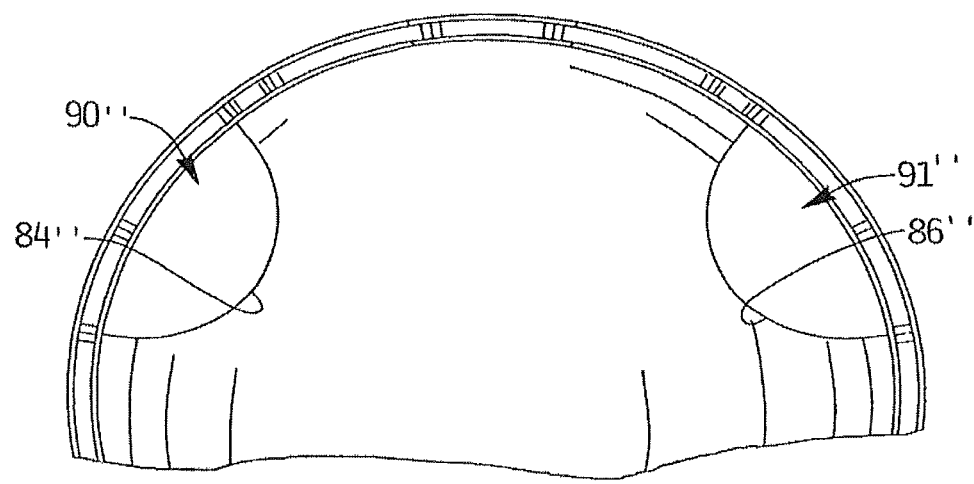
FIG. 6E is a top view of the upper region of an alternate embodiment of the membrane shown in the open position.
Figure 7A:
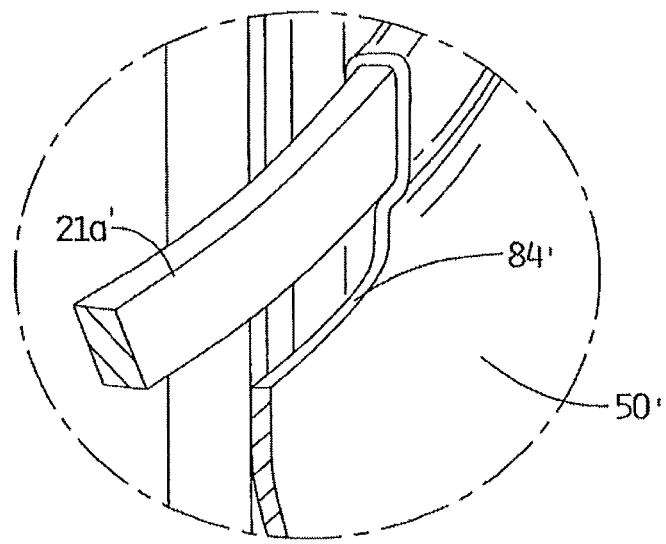
FIG. 7A is a cross-sectional view similar to FIG. 6B except showing the membrane of FIG. 7 in the closed position.
Figure 7:
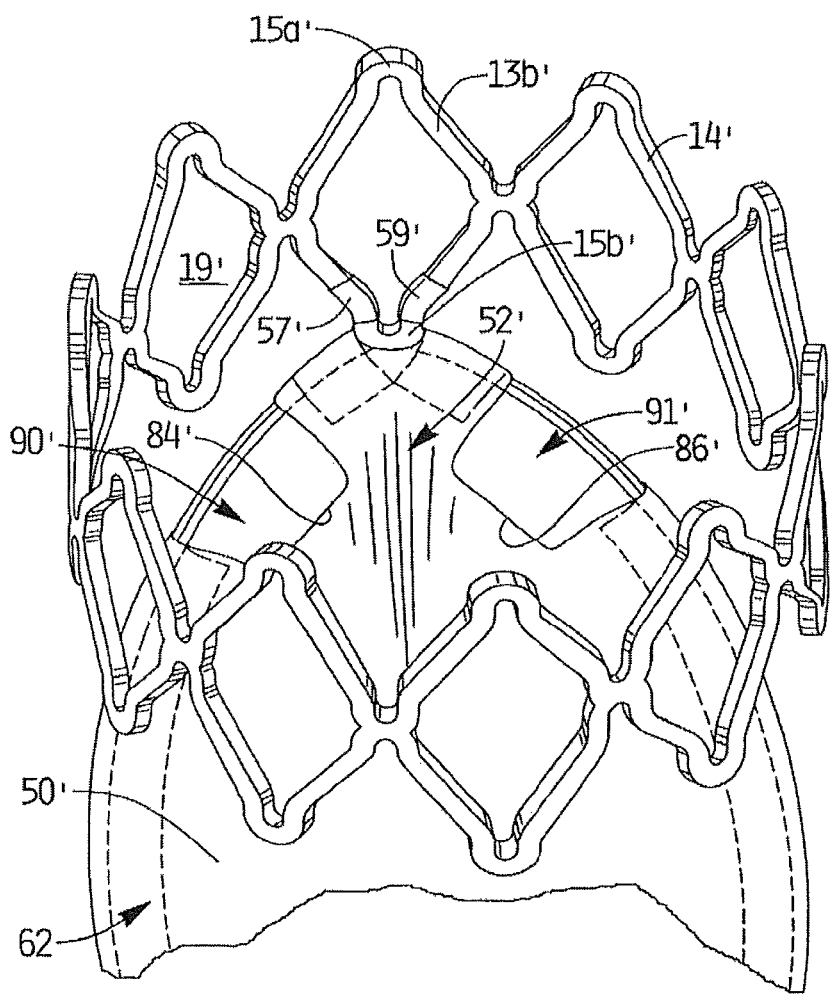
FIG. 7 is a view similar to FIG. 4 showing another alternate embodiment of the membrane with flaps forming larger openings for increased antegrade blood flow.

As can be appreciated, the body portion of the membrane 50 extends substantially if not entirely across the expanse of the vessel in the open position. However, the openings 90 and 91 adjacent the unattached flaps 84, 86 provide a sufficient gap for the necessary amount of blood flow, it being appreciated by applicants that a normally functioning valve is only open about 35%. In some embodiments, the openings in the membrane created by the space between flaps 84, 86 and the support create a space gap in the range of about 5% to about 15% of the diameter of the vessel. In the alternate embodiment depicted in FIG. 7, larger openings 90' and 91' are formed to allow more antegrade blood flow. In these large opening embodiments, a space (opening) can be created preferably representing about 15% to about 45%, and more preferably from about 15% to about 30% of the diameter of the vessel. (In all other respects the regulating device of FIG. 7 is identical to that of FIG. 4 and the corresponding parts are labelled by numerals with a prime designation and therefore are not discussed herein). These percentages are defined in terms of the diameter of the blood vessel. For example, if a rectangular opening is formed of dimension of 2 mm×4 mm, and is placed in a 10 mm vessel, the cross section occupied by the two openings (about 16 mm) would be about 20% of the overall diameter of the vessel (about 78 mm). It should be appreciated that the foregoing ranges and percentages are provided by way of example and other size openings creating a different percentage opening are also contemplated. Also, other shape openings can be provided other than rectangular, including square, semicircular, etc. FIG. 6E shows by way of example substantially semicircular openings 90", 91" formed by flaps 84", 86", respectively.

Figure 5A:
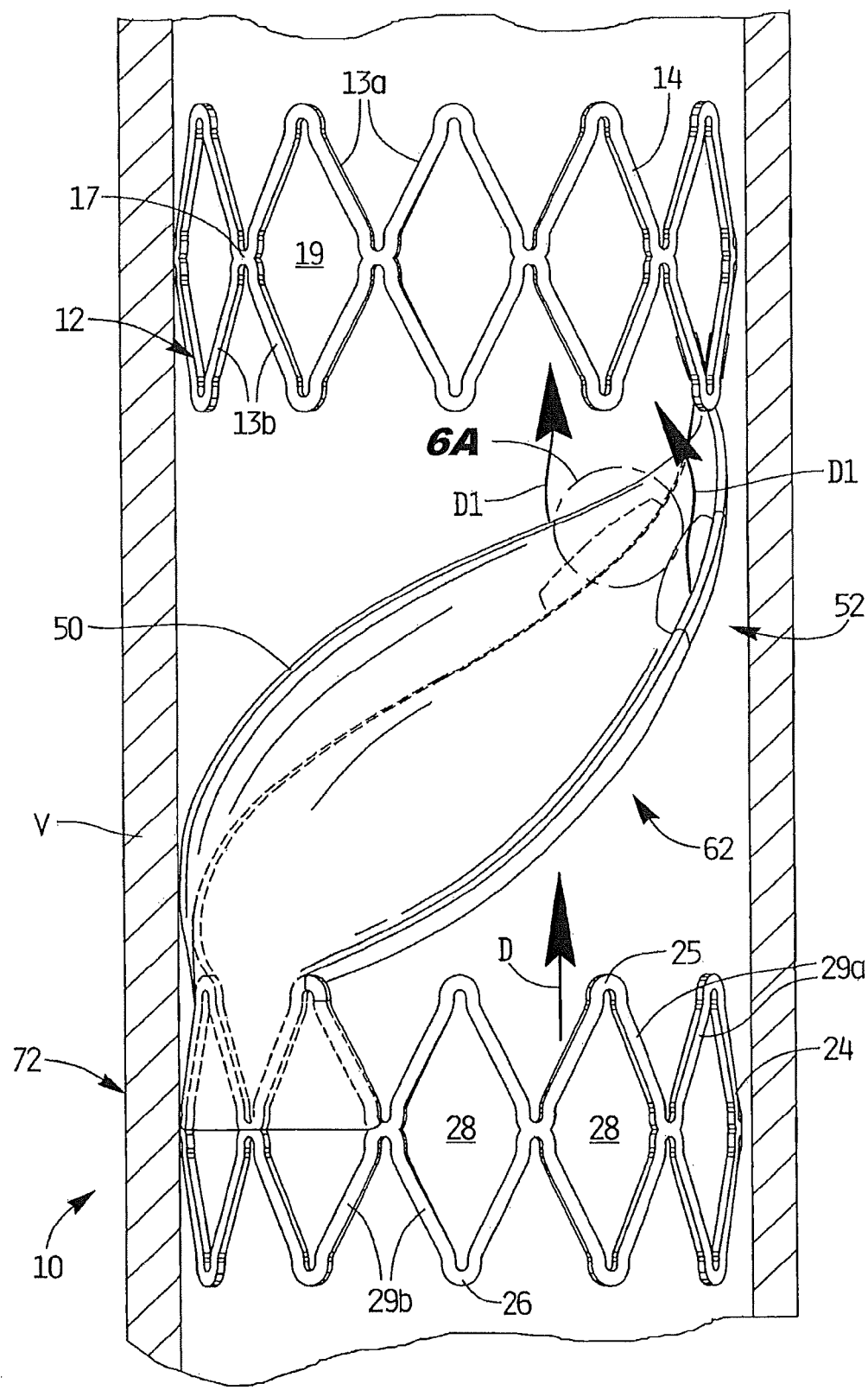
FIG. 5A is a side perspective view showing the membrane in the open position.
Figure 5B:
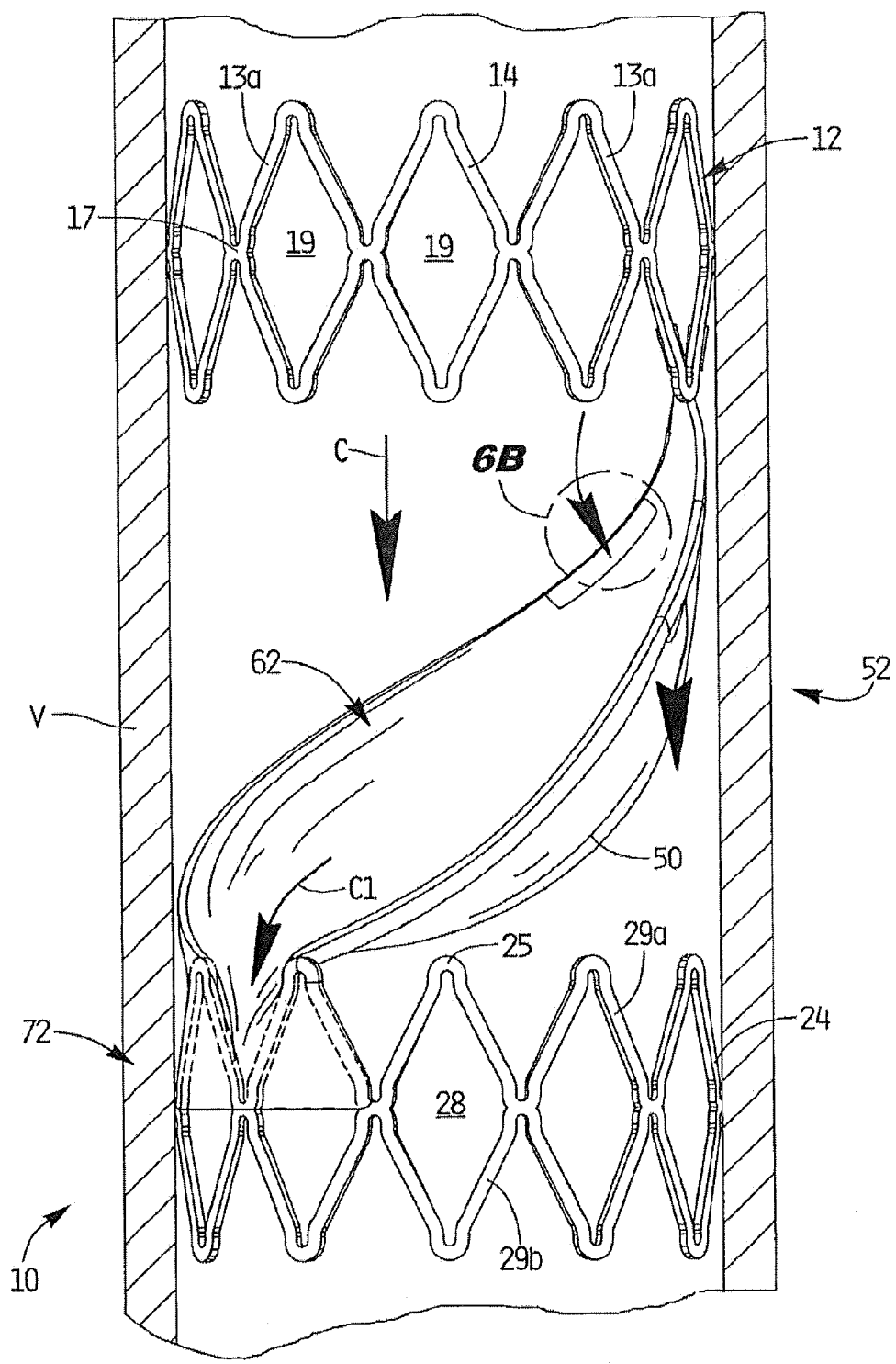
FIG. 5B is a side perspective view similar to FIG. 5A showing the membrane in the closed position.

Movement of the membrane 50 between an open (blood flow enabling) position/condition to allow antegrade blood flow and a closed (blood flow inhibiting position/condition) to essentially block flow are shown in respective FIGS. 5A and 5B, and shown in more detail in FIGS. 6A-6D. In the closed position, however, a minimal amount of blood flow is allowed as will be discussed below.

More specifically, and with reference to FIG. 5A, blood flowing through the blood vessel V in the downstream direction (antegrade flow) indicated by arrow "D" will act against the valve membrane 50 in such a manner as to push the body portion upwardly as viewed in the drawing, creating a concave belly on the underside. The blood will travel along the concave surface and up the membrane and the blood pressure will force the flaps 84 and 86 upwardly, separating (spreading) them from the respective connecting members 21a, 21b as also shown in FIGS. 6A and 6D to form an opening or gap.

After the pulsed blood travels in the direction of arrow D1 (FIG. 5A), through the openings (spaces) 90, 91, the blood backs up in the direction of arrow C of FIG. 5B. This retrograde blood flow will act against the angled body of the membrane 50, forcing it downwardly as viewed in FIG. 5B to form a convexity on its underside. This downward pressure will force flaps 84, 86 downwardly adjacent to the connecting members 21a, 21b, respectively, and against the connecting member as shown for example in FIGS. 6B and 6C, thus essentially closing the openings 90, 91 to prevent blood flow therethrough. However, a small amount of blood will force its way between the membrane 50 and the vessel wall as depicted by arrow C1 in FIG. 5B, thereby reducing stasis or stagnation that could lead to clotting. In embodiments wherein a larger flap is utilized to create a larger opening, such as in the embodiment of FIG. 7, the flap 84' (and 86', not shown) in the closed position would lie adjacent the connecting members, and extend underneath the connecting member (e.g. connecting member 21a') to lie against the vessel wall as shown in FIG. 7A, thereby inhibiting blood flow.

It should be appreciated that the membrane extends at an angle across the vessel of about 50 to about 70 degrees to help direct the blood flow and continuously wash the membrane body to prevent blood stagnation. (Other angles are also contemplated) More specifically, blood contacting the body portion of the membrane 50 in the open position will be directed upwardly, along the concave surface, thereby washing the membrane body to wash away clots to reduce the likelihood of clotting. In the closed position, blood contacting the membrane body will be directed downwardly along the angled body to wash the opposing side of the membrane to likewise reduce the likelihood of clotting.

As can be appreciated, the membrane 50 remains at substantially the same angle across the blood vessel in the open (flow allowing) and closed (flow inhibiting) positions/conditions. That is, as shown in FIGS. 5A and 5B, the upper region of the membrane 50 is adjacent one side of the vessel wall in the open (flow allowing) position. The upper region remains adjacent the same wall in the closed (flow inhibiting) position. Similarly, the lower region of the membrane 50 is adjacent an opposite side of the vessel wall, and remains adjacent that wall in both the open and closed positions of FIGS. 5A, 5B, respectively. Thus, the upper and lower attached regions of the membrane remain in substantially the same position.

Figure 8:
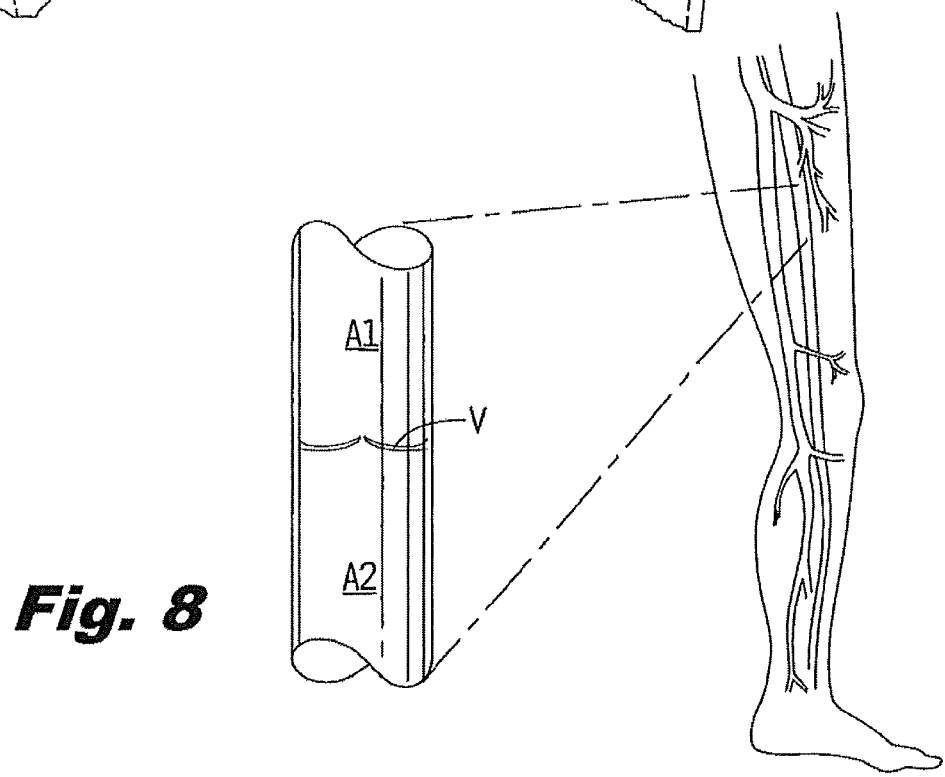
FIG. 8 is a drawing of the anatomy of the patient showing two examples of locations of placement of the flow regulating device.

One example of the location of placement of the flow regulating device in a patient's leg is shown in FIG. 8 with areas A1 and A2 showing possible placement sites of the device, e.g. upstream or downstream of the native valve V.

If composed of shape memory, the device will automatically expand to the position shown either upon release from a delivery member or in response to temperature change. However, if composed of other materials, the device can be designed to automatically expand due to the springiness of the material or can alternatively be implanted in a blood vessel using a balloon catheter (not shown) as described in copending U.S. patent application Ser. No. 11/801,691, the entire contents of which are incorporated herein by reference. That is, rings 14 and 24 can be moved from a closed position to an expanded position by inflating the balloon or by use of a mechanical expander. Upon expansion, the rings 14 and 24 apply a force against the vessel wall, thereby being retained therein. The balloon or mechanical expander is then deflated and the catheter is removed from the blood vessel so the device 10 can regulate the flow of blood through the vessel in the manner described above.

In the embodiments disclosed herein showing substantially circular rings, it should be understood that the rings can be shaped to have a size larger than the diameter of the vessel and therefore, depending on the size of the vessel, may not assume a circular shape but have an oval shape pressing against the vessel wall toward a circular configuration.

Referring now to FIGS. 9-11, there is shown a frame for a flow regulating device constructed in accordance with another preferred embodiment of the subject invention, and designated generally by reference numeral 200. Regulating device 200 includes an elongated frame 220 that consists of upper and lower substantially annular ring portions 240 and 260, much as described above. Rings 240 and 260 are connected to one another by at least one connective member 280 in the form of an x-shaped bar or wire. In the exemplary embodiment of FIGS. 9-14, two x-shaped connective members 280 are shown. Connective members 280 are adapted and configured to follow the circumference of the host vessel. The individual cross-linked bars or wires of each x-shaped connective member 280 are attached to the opposed rings 240 and 260 of frame 220 at locations that are about 180° apart from one another, making device 200 substantially symmetrical. This gives frame 220 an inherent symmetrical flexibility and enables it to move with the natural movements (e.g., pulsitile) of the vein.

FIGS. 12-14 show device 200 with the membrane, much as described above, in place. Membrane or sail 250 attaches to portions of the x-shaped connective members 280. Apertures 270 allow blood flow in one direction, and inhibit flow in the opposite direction much as described above. This frame and sail configuration gives device 200 more support and symmetry, allows for delivery using a simpler delivery device, distributes stress more evenly and reduces stress raisers between support portions.

Although the blood flow-regulating device of the subject invention has been described with respect to preferred embodiments, those skilled in the art will readily appreciate that changes and modifications may be made thereto without departing from the spirit and scope of the subject invention. While the above description contains many specifics, those specifics should not be construed as limitations on the scope of the disclosure, but merely as exemplifications of preferred embodiments thereof. Those skilled in the art will envision many other possible variations that are within the scope and spirit of the disclosure.

What is claimed is:

1. An implantable device for regulating blood flow through a blood vessel, comprising:
    a first frame and a second frame axially spaced-apart from the first frame, each frame configured to expand against an interior wall of a blood vessel and defining an opening for receiving blood flow therethrough;
    a linking member comprising at least two bar elements that couple the first frame to the second frame; and
    a valve membrane extending between the first frame and the second frame and comprising a first region adjacent to a second region, wherein the first region of the valve membrane attaches to and spans across a first bar element to a second bar element, and the second region of the valve membrane comprises at least two flaps being moveable between a first position to enable blood flow and a second position to inhibit blood flow.

2. The implantable device of claim 1, wherein the bar elements form an x-shape.

3. The implantable device of claim 2, wherein the bar elements are curved.

4. The implantable device of claim 1, wherein the valve membrane further comprises a third region adjacent to the second region.

5. The implantable device of claim 4, wherein the third region attaches to and spans across the first bar element and the second bar element.

6. The implantable device of claim 1, wherein the implantable device is formed at least in part from a shape memory alloy material.

7. The implantable device of claim 1, wherein the valve membrane is formed at least in part from ePTFE.

8. The implantable device of claim 1, wherein the valve membrane is coated at least in part with an anti-clotting agent.

9. The implantable device of claim 1, further comprising another linking member.

10. The implantable device of claim 9, wherein the linking members are substantially symmetrical to each other.

11. The implantable device of claim 1, wherein first and second bar elements are coupled to the first frame at the same location, and the first and second bar elements are coupled to the second frame at different locations.

12. An implantable device for regulating blood flow through a blood vessel, comprising:
    an elongate support dimensioned and configured to be implanted in a blood vessel, the support comprising a first annular frame and a second annular frame that is coupled to and axially spaced-apart from the first annular frame via a linking member, the linking member comprising at least two bar elements; and
    a valve membrane attached to the first annular frame at a first radial position and attached to the second annular frame at one or more other radial positions that are different from the first radial position, thereby extending across an inner portion of the elongate support, wherein a section of the valve membrane comprises at least two flaps being moveable between a first position to enable blood flow and a second position to inhibit blood flow.

13. The implantable device of claim 12, wherein the bar elements form an x-shape.

14. The implantable device of claim 13, wherein the bar elements are curved.

15. The implantable device of claim 12, wherein the valve membrane comprises a first region and a second region, wherein the first region attaches to and spans across one bar element to another bar element, and the second region comprises the at least two flaps.

16. The implantable device of claim 12, wherein the implantable device is formed at least in part from a shape memory alloy material.

17. The implantable device of claim 12, wherein the valve membrane is formed at least in part from ePTFE.

18. The implantable device of claim 12, wherein the valve membrane is coated at least in part with an anti-clotting agent.

19. The implantable device of claim 12, further comprising another linking member comprising at least two bar elements that couple the first frame to the second frame.

20. The implantable device of claim 19, wherein the linking members are substantially symmetrical to each other.

* * * * *